United States Patent
Washburn et al.

[11] Patent Number: 6,126,605
[45] Date of Patent: *Oct. 3, 2000

[54] ULTRASOUND COLOR FLOW DISPLAY OPTIMIZATION BY ADJUSTING DYNAMIC RANGE

[75] Inventors: Michael J. Washburn, New Berlin; Gary E. MacLeod, Menomonee Falls; Sean D. Lucas, Waukesha; David J. Muzilla, Mukwonago, all of Wis.

[73] Assignee: General Electric Company, Milwaukee, Wis.

[*] Notice: This patent is subject to a terminal disclaimer.

[21] Appl. No.: 09/224,342

[22] Filed: Dec. 31, 1998

[51] Int. Cl.[7] .................................................. A61B 8/02
[52] U.S. Cl. ................................................... 600/454
[58] Field of Search ........................... 600/437, 441–444, 600/447, 453–455; 382/56

[56] References Cited

U.S. PATENT DOCUMENTS

| | | | |
|---|---|---|---|
| 5,235,984 | 8/1993 | D'Sa | 600/443 |
| 5,347,600 | 9/1994 | Barnsley et al. | 382/56 |
| 5,718,229 | 2/1998 | Pesque et al. | 600/441 |
| 5,732,705 | 3/1998 | Yokoyama et al. | 600/443 |
| 5,735,797 | 4/1998 | Muzilla et al. | 600/441 |
| 5,993,392 | 11/1999 | Roundhill et al. | 600/447 |
| 6,017,309 | 1/2000 | Washburn et al. | 600/454 |

*Primary Examiner*—Marvin M. Lateef
*Assistant Examiner*—Ali M. Imam
*Attorney, Agent, or Firm*—McAndrews Held and Malloy; Christian G. Cabou; Phyllis Y. Price

[57] ABSTRACT

An ultrasound color flow imaging system is programmed to optimize display images of power and velocity by automatically adjusting thresholds and data compression by using histograms and samplings of color flow data.

21 Claims, 4 Drawing Sheets

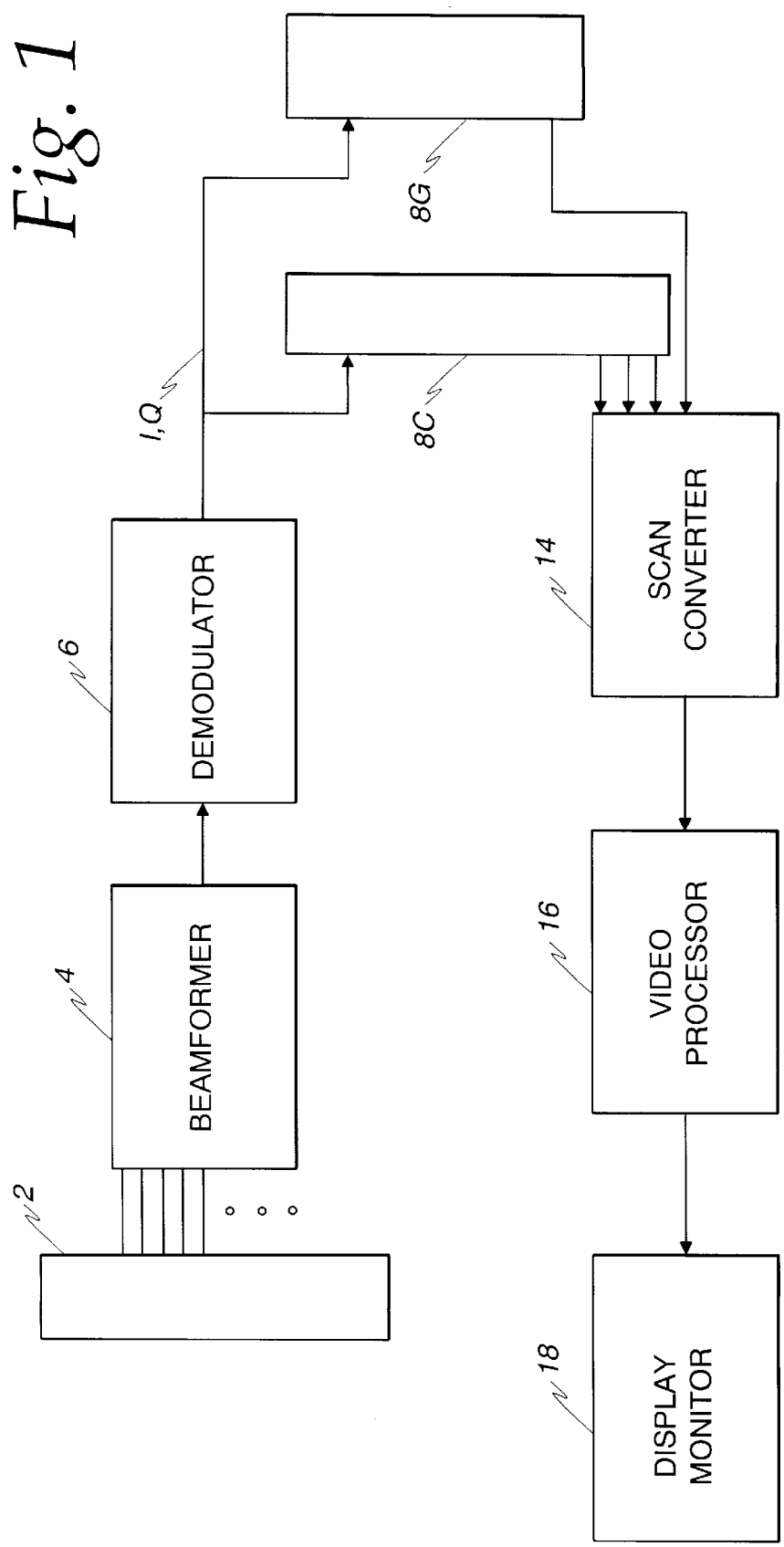

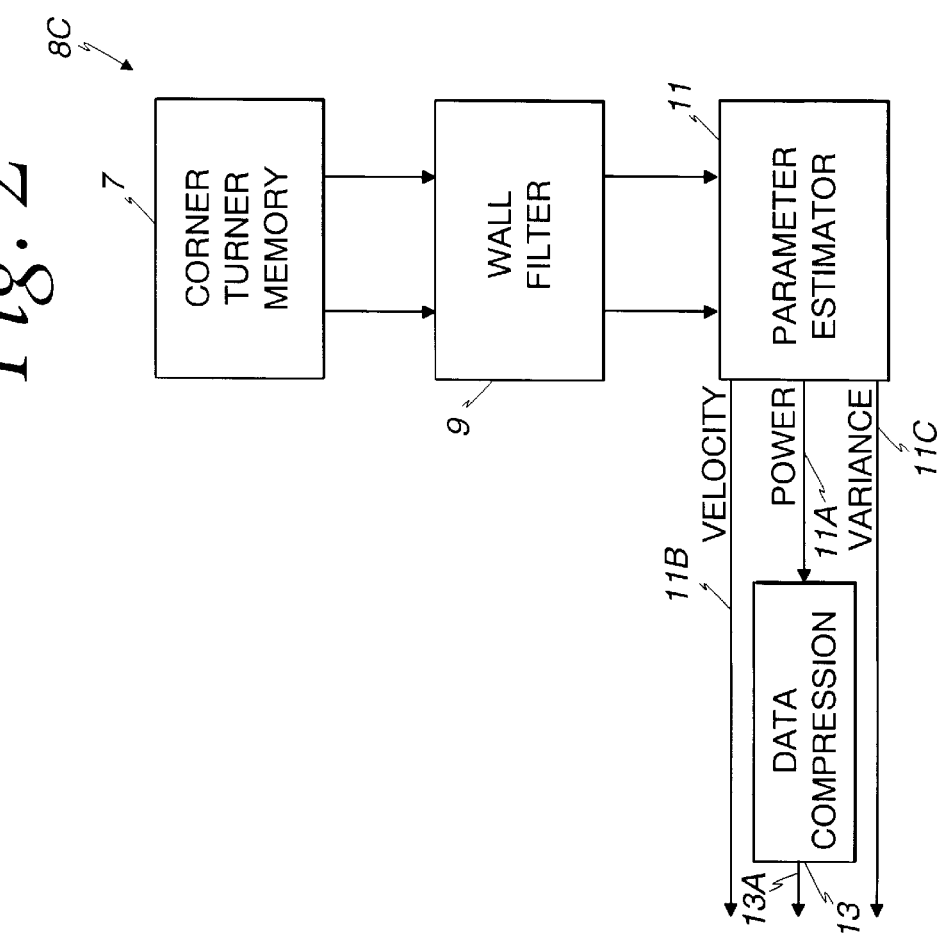

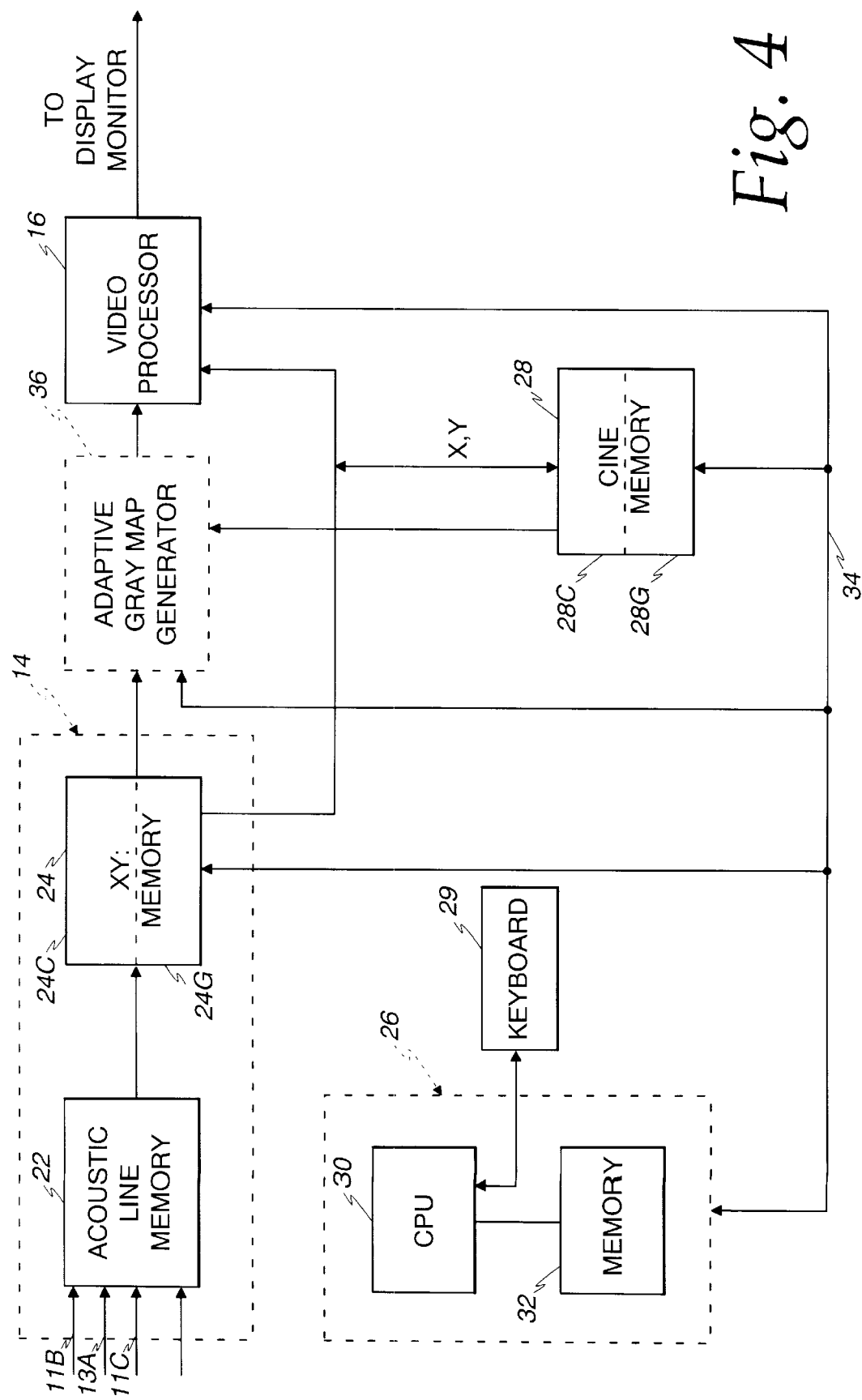

ULTRASOUND COLOR FLOW DISPLAY OPTIMIZATION BY ADJUSTING DYNAMIC RANGE

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

This invention generally relates to ultrasound color flow Doppler imaging of fluid flow fields. In particular, the invention relates to a method and an apparatus for improving the display of such imaging.

Ultrasonic scanners for detecting blood flow based on the Doppler effect are well known. Such systems operate by actuating an ultrasonic transducer array to transmit ultrasonic waves into the object and receiving ultrasonic echoes backscattered from the object. In the measurement of blood flow characteristics, returning ultrasonic waves are compared to a frequency reference to determine the frequency shift imparted to the returning waves by flowing scatterers such as blood cells. This frequency, i.e., phase shift, translates into the velocity of the blood flow. The blood velocity is calculated by measuring the phase shift from firing to firing at a specific range gate.

The change or shift in backscattered frequency increases when blood flows toward the transducer and decreases when blood flows away from the transducer. Color flow images are produced by superimposing a color image of the velocity of moving material, such as blood, over a black and white anatomical B-mode image. Typically, color flow mode displays hundreds of adjacent sample volumes simultaneously, all laid over a B-mode image and color-coded to represent each sample volume's velocity.

Typically, color flow processors estimate blood flow velocity, blood flow power, and blood flow variance. Typically, color flow data is used to modify the color of a region of interest on a display screen. The user selects the type of data used for the display. The modes typically available are power only, velocity only or velocity and variance combined.

In current ultrasound scanners, various color flow display parameters are either fixed with no user selectability or are preset to some specific setting and can only be changed if action is taken by the user, one parameter at a time. This limits image quality and user productivity for any given application and scanning situation. There is a need for a scanner in which these same parameters can all be automatically adjusted at the same time to optimize image quality related to color flow display for a specific scanning situation, thus increasing user productivity.

In the color flow power mode of operation, known ultrasound scanners typically provide a color flow dynamic range based on a compression curve preselected at the factory depending on the type of scanning application. For example, one dynamic range based on one compression curve is selected for scanning of the kidney, whereas another dynamic range based on another compression curve is selected for scanning of the carotid artery. Frequently, the actual scan data has a dynamic range different from the range upon which the compression curve is based. As a result, the dynamic range of the display is less than optimal. Accordingly, there is a need for a color flow ultrasound scanner which can automatically adjust for changes in the dynamic range of the received signals.

BRIEF SUMMARY OF THE INVENTION

This invention is useful in an ultrasound imaging system generating color flow signals in response to ultrasound signals backscattered from a subject under study. This aspect of the invention displays images in response to the color flow signals by storing first memory values in response to the color flow signals, preferably in a digital memory. A dynamic range compression scheme is determined based on an analysis of the first memory values, preferably by a logic unit. Second memory values are generated based on the dynamic range compression scheme and a color flow image is displayed in response to the second memory values, preferably by a color display unit.

By using the foregoing techniques, the display of an ultrasound imaging device can be automatically adjusted for changes in the dynamic range of the received signals.

BRIEF DESCRIPTION OF THE DRAWINGS

FIG. 1 is a schematic block diagram showing the signal processing chain for a conventional color flow and B-mode ultrasound imaging system.

FIG. 2 is a schematic block diagram showing the mid processor color flow apparatus illustrated in FIG. 1.

FIG. 3 is a schematic block diagram showing the mid processor B-mode apparatus illustrated in FIG. 1.

FIG. 4 is a schematic block diagram showing additional details of portions of the system illustrated in FIG. 1.

DETAILED DESCRIPTION OF THE INVENTION

Figure 5:
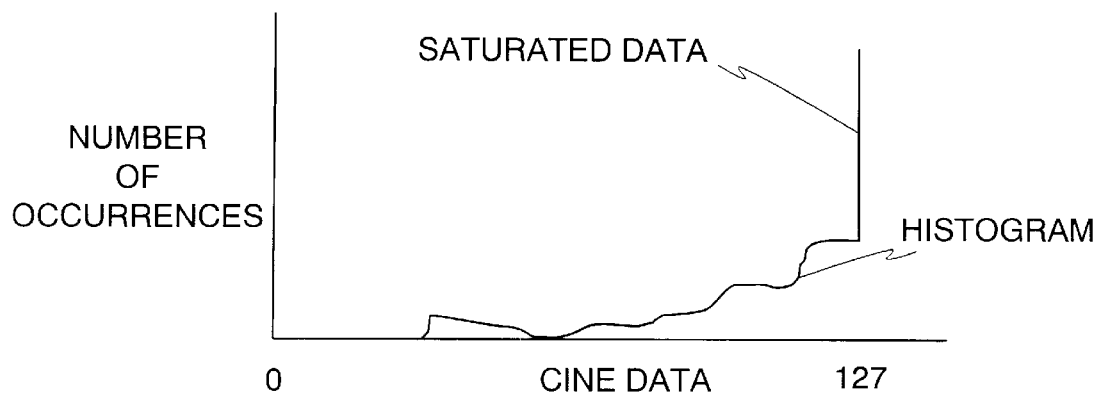
FIG. 5 is a graph illustrating one possible form of data stored in the cine memory shown in FIG. 4.

Referring to FIG. 1 the basic signal processing chain for a color flow and gray scale imaging system comprises an ultrasound transducer array 2, which is activated to transmit pulse sequences comprising tone bursts of length P which are fired repeatedly at a pulse repetition frequency (PRF) which typically is in the kilohertz range. The pulse sequences, including burst lengths P, are different for the color flow and B-mode processing. For color flow imaging, P may be 4 to 8 cycles, and the tone bursts are focused at the same transmit focal position with the same transmit characteristics.

A series of color flow transmit firings focused at the same transmit focal position are referred to as a "packet". Each transmit beam propagates through the object being scanned and is reflected by ultrasound scatterers in the object.

The return RF signals are detected by the transducer elements and received by the respective receive channels in the beamformer 4. The beamformer sums the delayed channel data and outputs in a beam summed signal which is demodulated into in-phase and quadrature (I/Q) signal components by a demodulator 6. The B-mode I, Q outputs from demodulator 6 are transmitted to a mid processor 8G for gray scale B-mode processing, and the color flow I, Q outputs from demodulator 6 are transmitted to a mid-processor 8C for color processing.

FIG. 2 illustrates mid-processor 8C. The I/Q signal components from demodulator 6 are stored in a corner turner memory 7, whose purpose is to buffer data from possibly interleaved firings and output the data as vectors of points across firings at a given range cell. Data is received in "fast time", or sequentially down range (along a vector) for each firing. The output of the corner turner memory is reordered into "slow time", or sequentially by firing for each range cell. The resultant "slow time" I/Q signal samples are passed through a wall filter 9 which rejects any clutter corresponding to stationary or very slow-moving tissue. The filtered outputs are then fed into a parameter estimator 11, which converts the range cell information into the intermediate autocorrelation parameters N, D and R(O). N and D are the numerator and denominator for the autocorrelation equation, as shown below:

$$N = \sum_{i=1}^{M-1} (I_i Q_{i+1} - I_{i+1} Q_i) \quad (2)$$

$$D = \sum_{i=1}^{M-1} (I_i I_{i+1} + Q_i Q_{i+1}) \quad (3)$$

where $I_i$ and $Q_i$ are the demodulated, basebanded input data for firing i, and M is the number of firings in the packet. R(O) is approximated as a finite sum over the number of firings in a packet, as follows:

$$R(O) = \sum_{i=1}^{M-1} \frac{(I_i^2 + Q_i^2 + I_{i+1}^2 + Q_{i+1}^2)}{2} \quad (4)$$

A processor converts N and D into a magnitude and phase for each range cell. The equations used are as follows:

$$|R(T)| = \sqrt{N^2 + D^2} \quad (5)$$

$$\phi(R(T)) = \tan^{-1}\left[\frac{N}{D}\right] \quad (6)$$

The parameter estimator processes the magnitude and phase values into signals having values representing estimates of power, velocity and turbulence or variance which are transmitted on conductors 11A, and 11B and 11C, respectively. The phase is used to calculate the mean Doppler frequency, which is proportional to the velocity as shown below; R(O) and |R(T)| (magnitude) are used to estimate the turbulence.

The mean Doppler frequency in hertz is obtained from the phase of N and D and the pulse repetition from T:

$$\bar{f} = \frac{1}{2\pi T}\tan^{-1}\left[\frac{N}{D}\right] = \frac{1}{2\pi T}(\phi(R(T))) \quad (7)$$

The mean velocity is calculated using the Doppler shift equation below. Since θ, the angle between the flow direction and the sampling direction, is not known, cos θ is assumed to be 1.0.

$$v = \frac{f}{f_o}\frac{c}{2\cos\theta} \quad (8)$$

Preferably, the parameter estimator does not calculate the mean Doppler frequency as an intermediate output, but calculates v directly from the phase output of the processor using a look-up table.

The turbulence may be calculated in the time domain as a second-order series expansion of the variance of the mean Doppler frequency. The time domain expression for turbulence involves calculating the zero-lag and one-lag autocorrelation functions, R(O) and R(T) respectively. The exact autocorrelation functions are approximated by finite sums over the known data in the number of firings in a packet:

$$\sigma^2 = \frac{2}{(2\pi T)^2}\left[1 - \frac{|R(T)|}{R(O)}\right] \quad (9)$$

The mean value signal θ (R(T)) is an estimate of the mean Doppler frequency shift of the flowing reflectors, which in turn is proportional to the mean blood flow velocity. The variance signal $\sigma^2$ indicates the frequency spread of the flow signal component of the baseband echo signal. This value is indicative of flow turbulence, since laminar flow has a very narrow range of velocities, while turbulent flow is a mixture of many velocities. To indicate the strength of the signal from the flowing reflectors, the signal R(O) indicates the amount of the returned power in the Doppler-shifted flow signal.

The signal power on conductor 11A is passed through a data compression module 13 which compresses the data according to families of data compression curves. A different family of curves can be provided for different scanning applications. For example, one family of curves is provided for renal scanning, while another family of curves is provided for carotid artery scanning. Typically, there are about three curves per family. The dynamic range of the signals is changed according to the curve used for the data compression. The curves in each family are arranged in order of increasing dynamic range. Controller 26 sets the default curve when a user selects the scan application. The dynamic range controls the range of intensities or lumens created on display 18.

Referring to FIG. 3, gray scale B-mode mid-processor 8G includes an envelope detector 10 for forming the envelope of the beamsummed receive signal by computing the quantity $(I^2+Q^2)^{1/2}$. The envelope of the signal undergoes some additional B-mode processing, such as logarithmic compression (block 12 in FIG. 3), to form display data which is output to the scan converter 14 (FIG. 1).

Referring again to FIG. 1, the color flow estimates and gray scale display data are sent to the scan converter 14, which converts the data into X-Y format for video display. The scan-converted frames are passed to a video processor 16, which basically maps the video data to a display color map and gray scale image frames for video display. The image frames are then sent to the video monitor 18 for display. Typically, for color images, either velocity or power are displayed alone or velocity is displayed in conjunction with either power or turbulence. System control is centered in a host computer (not shown), which accepts operator inputs through an operator interface (e.g., a keyboard) and in turn controls the various subsystems.

In general, for B-mode gray scale images, the display data is converted by the scan converter 14 into X-Y format for video display. The scan-converted frames are passed to the video processor 16, which maps the video data to a gray scale or mapping for video display. The gray scale image frames are then sent to the video monitor 18 for display.

The images displayed by the video monitor 18 are produced from an image frame of data in which each datum indicates the intensity or brightness of a respective pixel in the display. An image frame may, e.g., comprise a 256×256 data array in which each intensity datum is an 8-bit binary number that indicates pixel brightness. The brightness of each pixel on the display monitor 18 is continuously refreshed by reading the value of its corresponding element in the data array in a well-known manner. Each pixel has an intensity value which is a function of the backscatter cross section of a respective sample volume in response to interrogating ultrasonic pulses and the gray map employed.

Referring to FIG. 4, system control is centered in a master controller or host computer 26, which accepts operator inputs through an operator interface (not shown) and in turn controls the various subsystems. The master controller 26 also generates the system timing and control signals. The master controller 26 comprises a central processing unit (CPU) 30 and a random access memory 32. A keyboard 29 is used to enter data into CPU 30. The CPU 30 has read only memory incorporated therein for storing routines used in constructing gray and color maps based on acquired raw data.

The scan converter 14 comprises an acoustic line memory 22 and an X-Y memory 24. The B-mode and color mode intensity data stored in polar coordinate (R-θ) sector format in acoustic line memory 22 is transformed to appropriately scaled Cartesian coordinate pixel display data, which is stored in X-Y memory 24. The color data is stored in memory locations 24C, and the gray scale data is stored in memory locations 24G. The scan-converted frames are passed to video processor 16, which maps the data to a gray map for video display. The gray scale image frames are then sent to the video monitor for display.

Successive frames of acoustic sample data are stored in cine memory 28 on a first-in, first-out basis. Color frames are stored in memory locations 28C, and gray scale frames are stored in memory locations 28G. In the color region of interest, for every word of color data corresponding to a display pixel, there is a corresponding word of B-mode gray scale data corresponding to that pixel. The cine memory is like a circular image buffer that runs in the background, continually capturing acoustic sample data that is displayed in real time to the user. When the user freezes the system, the user has the capability to view acoustic sample data previously captured in cine memory.

The CPU 30 controls the XY memory 24 and the cine memory 28 via the system control bus 34. In particular, the CPU 30 controls the flow of raw data from the XY memory 24 to the video processor 16 and to the cine memory 28 and from the cine memory to the video processor 16 and to the CPU 26 itself. The CPU also loads the gray maps and color maps into the video processor.

Image frames are collected in cine memory 28 on a continuous basis. The cine memory 28 provides resident digital image storage for single image review and multiple image loop review and various control functions. The region of interest displayed during single-image cine replay is that used during the image's acquisition. The cine memory also acts as a buffer for transfer of images to digital archival devices (not shown) via the master controller 26.

The CPU 30 has random access memory for storing routines used in acquiring a raw data histogram, determining the end points of a new gray map input range, constructing a new gray map based on the end points of the new gray map input range, comparing the slope and gain of the new gray map to predetermined slope and gain limits, and if either limit is exceeded, reconstructing the new gray map to conform to the limit or limits.

In accordance with the preferred embodiments of the invention, the contrast of the ultrasound images is adjusted by the master controller 26 by creating a mapping of raw acoustic sample data into adjusted gray and color map values. First, the master controller 26 retrieves one or more image frames of raw data from the X-Y memory 24 or from the cine memory 28, storing that raw data in memory 32. The CPU 30 then compiles a histogram of the number of acoustic samples having an amplitude or value within each of a multiplicity of prescribed ranges or bins for the retrieved image frames of raw data.

According to the preferred embodiment, a color flow auto display processing mode is initiated by the user through keyboard 29 (FIG. 4) and can then be re-initiated by the user for updating of post-processing parameters or turned off altogether as the scanning situation changes.

The preferred embodiment uses the above-described B-mode gray scale and color flow scan data to optimize image quality of the color display. A composite histogram (histogram of the data over several frames) and/or a single frame histogram are constructed from the cine memory 28 data for color flow and/or B-mode by controller 26. Algorithms then are applied to the histogram results by controller 26 to determine how to properly adjust various parameters for a specific scanning situation or application.

By operating keyboard 29, the user may select the power only mode of color flow display (i.e., the PDI mode). According to the preferred embodiment, in the PDI mode, several discrete families of color flow dynamic range selections and data for corresponding compression curves are entered into memory 32 (FIG. 4). There is one family for each type of scanning application. For example, one family of dynamic range selections is used for ultrasound examination of the kidney, whereas another family of dynamic range selections is used for ultrasound examination of the carotid artery. In each family, there are three dynamic ranges available for automatic selection by the system. Each dynamic range is controlled by a different compression curve defined by digital data in memory 32.

The user enters the type of application on keyboard 29. In response, controller 26 presets the middle value dynamic range selection and corresponding compression curve which represents the typical dynamic range encountered when scanning the application selected by the user. The lower dynamic range in the family provides less dynamic range and the higher dynamic range in the family provides increased dynamic range compared to the middle dynamic range setting. Using the families of dynamic ranges, the auto dynamic range selection algorithm part of the auto color flow display processing mode automates dynamic range selection.

First, n frames of PDI color flow data are collected from cine memory 28C which represents the amplitude of the flow data present in the color flow region of interest (ROI) using the current preset dynamic range setting and compression curve. The n frames of data are required to account for flow pulsatility. Controller 26 executes the auto dynamic range selection algorithm which generates a first composite histogram of the data.

In the event the preset dynamic range is too low, a substantial percent of the data may be saturated at the maximum output value of 127. That is, the values are clustered in a range which is too high to create an optimum image on display monitor 18. Such a condition results in a first histogram of the type shown in FIG. 5. The auto dynamic range selection algorithm analyzes the first histogram, and, if at least x percent of the data is saturated at the maximum output value of 127 (i.e., condition 1 which is illustrated in FIG. 5), then the dynamic range is flagged as being too low, and the next higher dynamic range and corresponding compression curve stored in memory 32 are selected.

Figure 6:
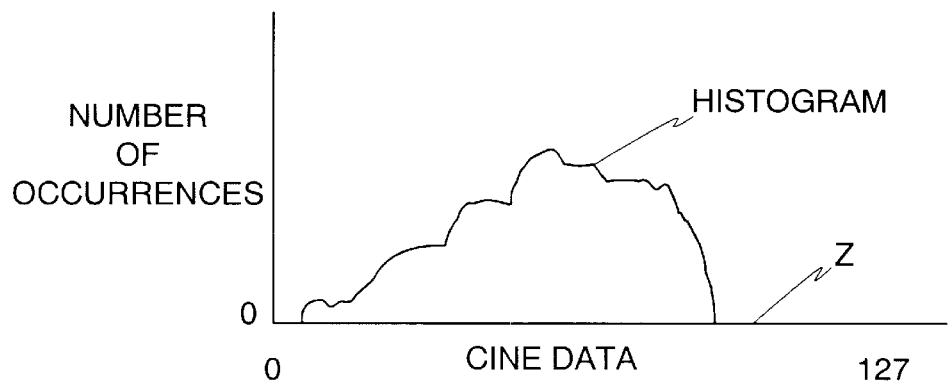
FIG. 6 is a graph showing another possible form of data stored in the cine memory shown in FIG. 4.

In the event the present dynamic range is too high, all of the data have values substantially below the maximum output value of 127. That is, all of the values are clustered in a range which is too low to create an optimum image on display monitor 18. Such a condition results in a first histogram of the type shown in FIG. 6. The auto dynamic range selection algorithm analyzes the first histogram, and, if less than t percent of the data occurs at output values between z and the maximum value of 127 (i.e., condition 2 which is illustrated in FIG. 6), then the dynamic range is flagged as being too high, and the next lower dynamic range and corresponding compression curve stored in memory 32 are selected.

Figure 7:
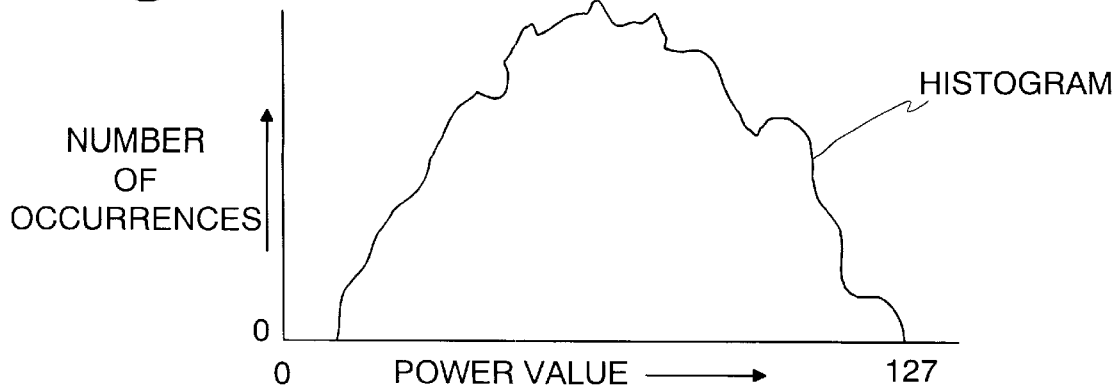
FIG. 7 is a graph showing another possible form of data resulting from use of the preferred form of the invention.

Based on the newly selected dynamic range and compression curve, the auto dynamic range selection algorithm calculates a second histogram based on the same data used to calculate the first histogram. The original dynamic range and compression curve are used to decompress the original data. The original data then is applied to the newly selected dynamic range and compression curve to create new compressed data in memory 32. The second histogram calculated from the new compressed data using the new dynamic range typically shows a spread of values more appropriate for optimum viewing on display monitor 18. Such an exemplary second histogram may be of the type shown in FIG. 7.

Alternatively, if more than three dynamic ranges and three compression curves per family are provided, the process may be repeated as new dynamic ranges and compression curves are selected. If the first histogram showed that the dynamic range was too low (i.e., condition 1 shown in FIG. 5), the process of selecting dynamic ranges and compression curves, decompressing the data, compressing the data using the newly selected curve and calculating second and subsequent histograms is repeated until y percent of the data or less is determined to be saturated (the condition shown in FIG. 7) or until the highest dynamic range setting is reached, effectively spreading the data out over more of the lower output values. If the original histogram showed that the dynamic range was too high (i.e., condition 2 shown in FIG. 6), the process of selecting dynamic ranges and compression curves, decompressing the data, compressing the data using the newly selected curve and calculating second and subsequent histograms is repeated until q percent of the data or more is determined to be between z and 127 (the condition shown in FIG. 7) or until the lowest dynamic range setting is reached, effectively spreading the data out over more of the higher output values.

As a second alternative, the first histogram may be used to calculate a new compression curve not previously stored which more nearly spreads the actual data over the dynamic range available for display. The new compression curve then is used to recompress the original data.

If neither condition 1 nor condition 2 is met, then the current dynamic range and compression curve are maintained.

As an alternative to the preceding steps, controller 26 forms a histogram of the PDI data before any dynamic range compression is applied or uncompresses the data and forms a histogram. Then the histogram of uncompressed PDI data is analyzed to determine its statistics, and an optimal dynamic range compression scheme is calculated. Various dynamic range compression curves such as logarithmic, cube root, S-curve, or others are optimally applied across the data based on the statistics of the histogram. This alternative preferably is implemented by a digital signal processor (DSP).

The user can choose to re-activate the color flow auto display processing mode, causing new data to be formed into a histogram, based on the current dynamic range setting, and causing the auto dynamic range selection algorithm to be re-employed. Or the user can turn off the color flow auto display processing mode, causing the current dynamic range setting to be maintained until the user changes the selection manually.

The embodiments described here can be extended to automatically adjust other post-processing parameters such as power thresholds, wall filter cutoffs, baseline shifts, and velocity scales. The same basic idea of collecting B and/or color flow frames of cine data would be applied and associated algorithms would be employed to determine exactly how to adjust the particular post processing parameter.

The foregoing preferred embodiments have been disclosed for the purpose of illustration. Variations and modifications of the concept of the invention will be readily apparent to persons skilled in the art. All such variations and modifications are intended to be encompassed by the claims set forth hereinafter.

What is claimed is:

1. In an ultrasound imaging system generating color flow signals in response to ultrasound signals backscattered from a subject under study, improved apparatus for displaying images in response to the color flow signals comprising in combination:

a memory connected to store first memory values in response to the color flow signals;

a logic unit connected to determine a dynamic range compression scheme based on an analysis of the first memory values and to generate second memory values based on the dynamic range compression scheme; and a display connected to display a color flow image in response to the second memory values.

2. Apparatus, as claimed in claim 1, wherein the first memory values are altered from the values of the color flow signals based on a second dynamic range compression scheme.

3. Apparatus, as claimed in claim 1, wherein the logic unit is connected to create the dynamic range compression scheme based on an algorithm which analyzes the first memory values.

4. Apparatus, as claimed in claim 1, wherein the first memory values equal the values of the color flow signals.

5. Apparatus, as claimed in claim 1, wherein the memory stores compression data defining first and second dynamic range compression schemes, wherein the logic unit determines the dynamic range compression scheme by selecting one of the first or second stored dynamic range compression schemes and wherein the first memory values are altered based on the selected dynamic range compression scheme.

6. Apparatus, as claimed in claim 5, wherein the first dynamic range compression scheme comprises a first type and the second dynamic ranges comprises a second type different from the first type.

7. Apparatus, as claimed in claim 5, wherein the first memory values are altered from the values of the color flow signals based on a third dynamic range compression scheme.

8. Apparatus, as claimed in claim 7, wherein the logic unit is connected to analyze the first memory values by decompressing the first memory values, analyzing the decompressed first memory values, selecting one of the first or second stored dynamic range compression schemes, altering the decompressed first memory values based on the selected dynamic range compression scheme to generate second memory values and enabling storage of the second memory values.

9. Apparatus, as claimed in claim 1, wherein the logic unit is connected to analyze the first memory values by generating a histogram of the first memory values.

10. Apparatus, as claimed in claim 1, wherein the first memory values represent power estimates calculated in response to the backscattered signals.

11. In an ultrasound imaging system generating color flow signals in response to ultrasound signals backscattered from a subject under study, an improved method for displaying images in response to the color flow signals comprising the steps of:

storing first memory values in response to the color flow signals;

determining a dynamic range compression scheme based on an analysis of the first memory values;

generating second memory values based on the dynamic range compression scheme; and displaying a color flow image in response to the second memory values.

12. A method, as claimed in claim 11, wherein the step of storing the first memory values comprises the step of altering the values of the color flow signals based on a second dynamic range compression scheme.

13. A method, as claimed in claim 11, wherein the step of determining a dynamic range compression scheme comprises the step of creating the dynamic range compression scheme by analyzing the first memory values.

14. A method, as claimed in claim 11, wherein the first memory values equal the values of the color flow signals.

15. A method, as claimed in claim 11, wherein the step of storing comprises the step of storing compression data defining first and second dynamic range compression schemes, wherein the step of determining a dynamic range compression scheme comprises the step of selecting one of the first or second stored dynamic range compression schemes and wherein the step of generating second memory values comprises the step of altering the values of the color flow signals based on the selected dynamic range compression scheme.

16. A method, as claimed in claim 15, wherein the first dynamic range compression scheme comprises a first type and the second dynamic ranges comprises a second type different from the first type.

17. A method, as claimed in claim 15, wherein the step of storing comprises the step of altering from the values of the color flow signals based on a third dynamic range compression scheme.

18. A method, as claimed in claim 17, wherein the step of selecting comprises the steps of:

decompressing the first memory values; and analyzing the decompressed first memory values.

19. A method, as claimed in claim 18, wherein the step of generating comprises the steps of:

altering the decompressed first memory values based on the selected dynamic range compression scheme to generate second memory values; and enabling storage of the second memory values.

20. A method, as claimed in claim 11, wherein the step of determining a dynamic range compression scheme comprises the step of analyzing the first memory values by generating a histogram of the first memory values.

21. A method, as claimed in claim 11, wherein the first memory values represent power estimates calculated in response to the backscattered signals.

* * * * *